(12) United States Patent
Chouzier et al.

(10) Patent No.: US 8,846,975 B2
(45) Date of Patent: Sep. 30, 2014

(54) PROCESS FOR PREPARING DICARBOXYLIC ACIDS

(75) Inventors: Sandra Chouzier, Lyons (FR); Gérard Mignani, Lyons (FR); Simon Rousseau, Gradignan (FR); Flavie Sarrazin, Talence (FR); Sergio Mastroianni, Lyons (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/697,189

(22) PCT Filed: May 9, 2011

(86) PCT No.: PCT/EP2011/057381
§ 371 (c)(1),
(2), (4) Date: Dec. 11, 2012

(87) PCT Pub. No.: WO2011/141404
PCT Pub. Date: Nov. 17, 2011

(65) Prior Publication Data
US 2013/0109886 A1 May 2, 2013

(30) Foreign Application Priority Data
May 10, 2010 (FR) .................................... 10 53628

(51) Int. Cl.
*C07C 51/27* (2006.01)
*C07C 51/31* (2006.01)

(52) U.S. Cl.
CPC .................................. *C07C 51/316* (2013.01)
USPC .......................................... 562/528; 562/530

(58) Field of Classification Search
CPC .................................................... C07C 51/316
See application file for complete search history.

(56) References Cited

U.S. PATENT DOCUMENTS

| 2,298,387 | A | * | 10/1942 | Kenyon et al. | ................. | 554/132 |
| 3,076,026 | A | | 1/1963 | White | | |
| 3,444,194 | A | * | 5/1969 | Minisci et al. | ................. | 562/528 |
| 4,259,524 | A | * | 3/1981 | Ando et al. | ................... | 562/526 |

FOREIGN PATENT DOCUMENTS

| DE | 767 840 | 8/1954 |
| DE | 68 897 | 9/1969 |
| FR | 1 346 615 A | 12/1963 |
| GB | 1 296 447 | 11/1972 |

OTHER PUBLICATIONS

International Search Report issued on Sep. 14, 2011, by the European Patent Office as the International Searching Authority in International Patent Application No. PCT/EP2011/057381.
Castellan et al., "Industrial Production and Use of Adipic Acid," Catalysis Today, 1991, pp. 237-254, vol. 9.
Castellan et al., "Nitric Acid Reaction of Cyclohexanol to Adipic Acid," Catalysis Today, 1991, pp. 255-283, vol. 9.
Castellan et al., "Synthesis of Adipic Acid Via the Nitric Acid Oxidation of Cyclohexanol in a Two-Step Batch Process," Catalysis Today, 1991, pp. 285-299, vol. 9.
Castellan et al., "Synthesis of Adipic Acid Via Nitric Acid Oxidation of Cyclohexanol in a Two-Step Continuous Process," Catalysis Today, 1991, pp. 301-322, vol. 9.
English language translation of the Written Opinion of the International Searching Authority issued on Nov. 13, 2012, in International Patent Application No. PCT/EP2011/057381.

* cited by examiner

*Primary Examiner* — Paul A Zucker
(74) *Attorney, Agent, or Firm* — Dentons US LLP

(57) ABSTRACT

A process for preparing dicarboxylic acids is described. More particularly a process is described for preparing adipic acid (1,6-hexanedioic acid), by the action of nitric acid, starting from cyclic ketones or alcohols which are the corresponding compounds from the standpoint of the number of carbon atoms, in the presence of one or more oxides of nitrogen at a molar concentration in the reaction mixture of greater than 2.5 mmol per kg of reaction mixture.

19 Claims, No Drawings

PROCESS FOR PREPARING DICARBOXYLIC ACIDS

CROSS-REFERENCE TO PRIOR APPLICATIONS

This application is a National Stage of PCT/EP2011/057381, filed May 9, 2011, and designating the United States (published in French on Nov. 17, 2011, as WO 2011/141404 A1; the title and abstract were published in English), which claims priority to FR 10/53628, filed May 10, 2010, each hereby expressly incorporated by reference in its entirety and each assigned to the assignee hereof.

The present invention relates to a process for preparing dicarboxylic acids, more particularly adipic acid (1,6-hexanedioic acid), by the action of nitric acid, starting from cyclic ketones or alcohols which are the corresponding compounds from the standpoint of the number of carbon atoms, in the presence of one or more oxides of nitrogen at a substantial molar concentration in the reaction mixture.

Adipic acid is an important intermediate, particularly in the field of polymers and more particularly for the preparation of polyamide, for example polyamide 6-6, or polyurethanes. For the applications of polyamide 6-6, it is necessary to have a very high purity and for this purity to be already present at the stage of the precursors, particularly at the stage of adipic acid. The requirement of maximum purity is particularly acute when the adipic acid is to serve as raw material for the textile, electronics or agrifood industries.

Accordingly, whether for the production of polyamide 6-6 or for other applications, such as the production of certain polyurethanes, the purity of the adipic acid employed must be extremely high, in terms both of amounts of organic by-products and of amounts of metallic residues. Specifically, the adipic acid must not contain impurities, especially metallic impurities, at a concentration of more than 1 ppm.

Castellan et al. (*Catalysis Today*, 9 (1991) 237-322) provide a wide review of the issues associated with adipic acid, more particularly those associated with its preparation by the action of nitric acid in the presence of oxidation catalysts such as vanadium and copper.

Specifically, adipic acid is conventionally synthesized by oxidation using nitric acid of a mixture of cyclohexanone and cyclohexanol in the presence of oxidation catalysts such as copper and vanadium.

The employment of such catalysts presents major disadvantages, associated with the cost of using them, with the need to recycle them in subsequent steps, with the need to purify the products formed, or else the need to employ supplementary steps of washing and crystallization.

Despite this, in the absence of such catalysts, the direct reaction of nitric acid results primarily in the formation of stable nitrogen derivatives ($N_2$, $N_2O$), which are therefore difficult to re-oxidize, and also in a poor selectivity for adipic acid, owing to the formation of other dicarboxylic acids such as glutaric acid and succinic acid, as described by Castellan et al. (supra).

Hence the known processes present major disadvantages, including, quite particularly, the employment of catalysts.

Moreover, nitric oxidation by nitric acid or by oxides of nitrogen of compounds such as cyclohexanol gives rise to nitrous vapours. These vapours are produced in an amount which is difficult to control and cannot be exploited to any great extent, since it is dependent on the conditions under which the reaction is employed (temperature, nature and purity of the substrate to be oxidized, etc.). It is known practice, therefore, to remove these vapours as they are formed, as disclosed in document DE-767840.

The present invention therefore proposes providing an improved process for employing the reaction of nitric oxidation in order to produce dicarboxylic acids from cyclic ketones or alcohols having the same number of carbon atoms, in the presence of a significant amount of oxides of nitrogen, which allows some or all of the problems of the prior-art processes to be resolved.

The process according to the invention is specifically a process which does away with the presence of catalyst and makes it possible, therefore, to reduce the costs associated with the purification of the resultant dicarboxylic acid, particularly with regard to the amount of residual metals. It also makes it possible to avoid the costs associated with the catalyst recycling operations. Therefore, because of the absence of catalyst, the process according to the invention is also a process which is more environment-friendly.

The process according to the invention makes it possible, furthermore, to consume or recycle the oxides of nitrogen that are formed, to retain a particularly high selectivity for adipic acid, often of the order of or greater than 90%, in particular greater than 95%, to obtain high dicarboxylic acid yields, which may reach or exceed 90%, more particularly 95%, after 5 minutes, and to allow low reactant residence times. This selectivity is obtained irrespective of the starting compound to be oxidized. The process according to the invention thus allows the aforementioned values for selectivity for adipic acid to be attained starting from cyclohexanol, from cyclohexanone or from a mixture of the two compounds.

The process of the invention can also be employed at lower temperatures than the known processes.

The process according to the invention also allows the reaction to be initiated or conducted in the presence solely of cyclohexanone in the preparation of adipic acid.

The process according to the invention may also be a continuous or batchwise process for preparing dicarboxylic acids.

The present invention therefore first provides a process for preparing a dicarboxylic acid of formula (I),

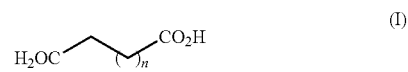

in which n represents an integer from 1 to 9, by action of nitric acid, in the presence of one or more oxides of nitrogen at a molar concentration in the reaction mixture of greater than 2.5 mmol per kg of reaction mixture, on the compounds of formula (II) or (III) in which n represents the same integral number as in the formula (I)

According to another aspect of the invention, the process employs a mixture of the compounds of formula (II) and (III).

According to another aspect of the invention, the process according to the invention is employed for the preparation of a compound of formula (I) for which n represents 2, 3, 4, 5 or 9; preferably 3 or 9; more particularly, n represents 3.

The process according to the invention employs nitric acid, usually in aqueous solution, in amounts of the order of 30% to 70% by mass, preferably of the order of 50% to 60% by mass, in the reaction mixture, and preferably of the order of 50% by mass in the reaction mixture.

The phrase "in the presence of one or more oxides of nitrogen at a molar concentration in the reaction mixture of greater than" means, for the purposes of the present invention, that one or more oxides of nitrogen are added to the reaction mixture in an amount corresponding to this molar concentration. This molar concentration is independent of the amount of nitrous vapours which may form during the nitric oxidation of the compounds of formula (II) and/or (III) in the presence of nitric acid.

According to another aspect of the invention, the process employs one or more oxides of nitrogen selected from NO, $NO_2$, $N_2O_3$, $N_2O_4$, $N_2O_5$, $NO_3$, $N_2O_6$, $N_4O$ and mixtures thereof, preferably from NO and $NO_2$.

According to a preferred aspect of the invention, the process employs one or more oxides of nitrogen in an amount of greater than 30 mmol of oxides of nitrogen per kg of reaction mixture.

According to another aspect of the invention, the process employs one or more oxides of nitrogen in an amount of from 2.5 to 1000 mmol of oxides of nitrogen per kg of reaction mixture, in particular of from 30 to 1000 mmol of oxides of nitrogen per kg of reaction mixture, preferably of from 30 to 850 mmol of oxides of nitrogen per kg of reaction mixture, more preferably of from 85 to 700 mmol of oxides of nitrogen per kg of reaction mixture, more preferably still of from 180 to 650 mmol of oxides of nitrogen per kg of reaction mixture. With particular advantage, the amount of oxides of nitrogen added is from 300 to 400 mmol/kg of reaction mixture.

According to one particularly advantageous embodiment of the invention, the process employs a molar ratio R, corresponding to the number of moles of oxides of nitrogen added to the reaction mixture relative to the number of moles of substrate to be oxidized (compounds (II) and/or (III)), which is greater than or equal to 0.5, in particular greater than or equal to 1, preferably greater than or equal to 1.5, and more preferably greater than or equal to 2. From a molar ratio of greater than or equal to 0.5, the selectivity for dicarboxylic acid is improved. This effect is even greater when the ratio R is greater than or equal to 1, and in particular to 1.5. The upper limiting value is, for reasons of economics and implementation, less than or equal to 50, preferably less than or equal to 30, in particular less than or equal to 10.

According to another aspect of the invention, the process employs one or more oxides of nitrogen in gaseous form.

According to another aspect of the invention, the process employs $NaNO_2$ as source of oxide of nitrogen.

The process of the invention employs the compounds of formula (II) and/or (III) in a reaction in a single step, leading directly and predominantly to the dicarboxylic acid of formula (I). This process has the advantage of not requiring separation of synthesis intermediates, in contrast to the process described in U.S. Pat. No. 3,076,026.

As indicated above, the process according to the invention is implemented preferably in the absence of metallic oxidation catalyst. This embodiment represents a highly advantageous embodiment because, while allowing a highly satisfactory selectivity for adipic acid to be attained, this absence makes it possible to reduce the costs associated with the purification of the resulting dicarboxylic acid, particularly in respect of the amount of residual metals. It also makes it possible to avoid the costs associated with catalyst recycling operations. Accordingly, owing to the absence of catalyst, the process according to the invention is also a process which is more environment-friendly.

The process according to the invention may also employ an oxidation catalyst, without jeopardizing the advantages of the process. The possible presence of such a catalyst may further improve the efficacy of the process according to the invention.

Accordingly, according to another aspect of the invention, the process further employs an oxidation catalyst, which may be selected from metallic catalysts. The catalyst may advantageously be selected from those comprising an element from the group consisting of Cu, Ag, Au, Mg, Ca, Sr, Ba, Zn, Cd, Hg, Al, Sc, In, Tl, Y, Ga, Ti, Zr, Hf, Ge, Sn, Pb, V, Nb, Ta, Cr, Mo, W, Mn, Tc, Re, Fe, Ru, Os, Co, Rh, Ir, Ni, Pd, Pt, lanthanides such as Ce, and combinations thereof.

When they are employed, these catalytic elements are employed either in the form of compounds, which advantageously are at least partly soluble in the liquid oxidation mixture under the conditions in which the oxidation reaction is employed, or supported, absorbed or bound to an inert support such as silica or alumina, for example.

When it is used, the catalyst is preferably soluble in one of these mixtures at ambient temperature or at the temperature at which these mixtures are recycled to a further oxidation. The term "soluble" means that the catalyst is at least partly soluble in the mixture in question. In the case of heterogeneous catalysis, the catalytically active metallic elements are supported or incorporated in a microporous or mesoporous organic matrix or in a polymeric matrix, or are in the form of organometallic complexes bound to an organic or inorganic support. By "incorporated" is meant that the metal is an element of the support or that complexes trapped sterically in porous structures are used under the conditions of the oxidation.

According to another aspect of the invention, the catalyst may be present at concentrations of metal in the liquid oxidation mixture of from 0.00001% to 5% by weight, for example of from 0.001% to 2% by weight.

According to another aspect of the invention, the process is employed at a temperature of from 20 to 150° C., preferably of from 30 to 100° C., more preferably of from 50 to 90° C., for example at 50° C. or at 70° C.

According to another aspect of the invention, the process is employed at atmospheric pressure. However, it is generally employed under pressure in order to maintain the components of the reaction mixture in liquid form. Accordingly, the pressure may be from 1 to 200 bar, preferably from 1 to 100 bar.

According to another aspect of the invention, the process is employed at a total pressure in the mixture of from 1 to 30 bar, preferably of from 1 to 15 bar, more preferably of from 1 to 4 bar.

The process according to the invention is typically conducted in aqueous medium.

According to another aspect of the invention, the dicarboxylic acids formed, particularly adipic acid, are recovered from the aqueous phase by crystallization, for example. The dicarboxylic acids thus recovered are advantageously purified in accordance with the techniques which are customary and are described in numerous documents. Among the purification processes, purification by recrystallization from various solvents such as water, aqueous acetic acid solutions or alcohols is preferred.

The process according to the invention may advantageously be employed within a larger process for the preparation of a dicarboxylic acid from a hydrocarbon, more particularly a cycloaliphatic or arylaliphatic hydrocarbon, for example cyclohexane or cyclododecane. In this case the hydrocarbon is oxidized to form an alcohol or a ketone, which are subsequently oxidized to form the dicarboxylic acid according to the invention. Thus the process according to the invention allows linear dicarboxylic acids, for example adipic acid or dodecanoic acid, to be prepared from cyclohexane or from cyclododecane.

The examples which follow illustrate the process of the invention, more particularly the advantages of this process.

EXAMPLES

1. Procedure
    A 68% nitric acid solution is prepared with 350 ppm of vanadium and 5400 ppm of copper; another 68% solution is prepared without copper or vanadium.
    Time to: 2.6 ml of one of the two nitric acid solutions are introduced into a 20 ml vial. The vial is then closed with a stopper equipped with a septum, and is stirred and heated at a temperature T (see values in Table 1).
    Time to+30 minutes: 0.28 ml of a sodium nitrite ($NaNO_2$) solution is injected through the septum, producing a molar amount of oxides of nitrogen in the reaction mixture at the concentration $C(NO_x)$ in mmol per kg (see values in Table 1).
    Time to+60 minutes: 0.5 ml of an 8% solution of cyclohexanone in water (called One), or a 4% solution of cyclohexanol in water (called Ol), or a 2%/2.2% cyclohexanol/cyclohexanone mixture (called Ol/One), is injected through the septum.
    Time to +60 minutes+reaction time tr: a sample of the reaction mixture is taken through the septum, and is soaked with cold water and analysed by HPLC chromatography to quantify the amounts of dicarboxylic acids produced and of substrate (cyclohexanone and/or cyclohexanol) consumed.
2. Definition of the Variables Calculated
    DC: degree of conversion of cyclohexanone (molar %):

$$DC = \frac{Ncyclohexanone(\text{initial}) - Ncyclohexanone(tr)}{Ncyclohexanone(\text{initial})} \times 100$$

Yld: yield of adipic acid (molar %):

$$Yld = \frac{Nadipic\ acid(tr)}{Ncyclohexanone(\text{initial})} \times 100$$

Selectivity: proportion of adipic acid formed relative to the three dicarboxylic acids assayed: succinic, glutaric and adipic acids (molar %):

$$Selectivity = \frac{Nadipic\ acid(tr)}{Nsuccinic\ acid(tr) + Nglutaric\ acid(tr) + Nadipic\ acid(tr)} \times 100$$

R: ratio of the number of moles of oxides of nitrogen added to the reaction mixture relative to the number of moles of substrate to be oxidized:

$$R = \frac{NNOx(\text{initial})}{Ncyclohexanone(\text{initial})}$$

Nx(t) represents the number of moles of the compound x in the reaction mixture at the time t.

NB: the DC, Yld and R for the other types of substrate, namely the cyclohexanol or the cyclohexanol/cyclohexanone mixture, are calculated in the same way as above, the Ncyclohexanone being replaced by Nsubstrate.

3. Results

The results in the presence and absence of catalysts, for different temperatures T, concentrations of oxides of nitrogen added $C(NO_x)$, type of substrate and reaction time tr are set out in Tables 1 to 7 below:

Influence of Catalyst Presence

TABLE 1

| No. | Presence of Cu and V | Substrate injected | $C(NO_x)$ (mmol/kg) | R | T (° C.) | tr (min) | DC (mol %) | Yld (mol %) | Selectivity (mol %) |
|---|---|---|---|---|---|---|---|---|---|
| 1 | yes | One | 0 | 0 | 70 | 60 | 100 | 26 | 69 |
| 2 | yes | One | 2.75 | 0.03 | 70 | 60 | 100 | 54 | 70 |
| 3 | yes | One | 28 | 0.31 | 70 | 60 | 100 | 57 | 82 |
| 4 | yes | One | 350 | 3.89 | 50 | 4 | 100 | 81 | 98 |
| 5 | no | One | 182 | 1.95 | 70 | 60 | 100 | 77 | 92 |
| 6 | no | One | 350 | 3.89 | 50 | 5 | 100 | 89 | 97 |
| 7 | no | One | 650 | 7.79 | 70 | 60 | 100 | 85 | 93 |

Comparing tests 4 and 6, it is noted that the presence of catalyst is not necessary for attaining a highly satisfactory selectivity for adipic acid (greater than 90%).

Influence of Substrate Type

TABLE 2

| No. | Presence of Cu and V | Substrate injected | C(NO$_x$) (mmol/kg) | R | T (° C.) | tr (min) | DC (mol %) | Yld (mol %) | Selectivity (mol %) |
|---|---|---|---|---|---|---|---|---|---|
| 6 | no | One | 350 | 3.89 | 50 | 5 | 100 | 89 | 97 |
| 8 | no | OI/One | 350 | 7.34 | 70 | 60 | 100 | 95 | 95 |
| 9 | no | OI | 350 | 7.94 | 70 | 10 | 100 | 95 | 96 |

It is found that, irrespective of the type of substrate, a selectivity of greater than or equal to 95% is obtained.

Effect of Temperature

TABLE 3

| No. | Presence of Cu and V | Substrate injected | C(NO$_x$) (mmol/kg) | R | T (° C.) | tr (min) | DC (mol %) | Yld (mol %) | Selectivity (mol %) |
|---|---|---|---|---|---|---|---|---|---|
| 6 | no | One | 350 | 3.89 | 50 | 5 | 100 | 89 | 97 |
| 10 | no | One | 350 | 3.89 | 20 | 60 | 100 | 82 | 95 |
| 9 | no | OI | 350 | 7.94 | 70 | 10 | 100 | 95 | 96 |
| 11 | no | OI | 350 | 7.94 | 20 | 60 | 100 | 78 | 93 |

It is noted that the process of the invention allows a selectivity of greater than 90% to be attained, even at ambient temperature. The reaction is quicker when the temperature is greater than or equal to 50° C.

Influence of the Amount of NOx Added:

With Catalyst: Comparing tests 1 to 4 in Table 1 above, it is found that, in the presence of catalyst, the selectivity increases more as the amount of NOx added goes up.

Without Catalyst/One

TABLE 4

| No. | Presence of Cu and V | Substrate injected | C(NO$_x$) (mmol/kg) | R | T (° C.) | tr (min) | DC (mol %) | Yld (mol %) | Selectivity (mol %) |
|---|---|---|---|---|---|---|---|---|---|
| 12 | no | One | 2.75 | 0.03 | 70 | 60 | 100 | 39 | 49 |
| 17 | no | One | 30 | 0.31 | 70 | 60 | 100 | 60 | 64 |
| 5 | no | One | 182 | 1.95 | 70 | 60 | 100 | 77 | 92 |
| 6 | no | One | 350 | 3.89 | 50 | 5 | 100 | 89 | 97 |
| 7 | no | One | 650 | 7.79 | 70 | 60 | 100 | 85 | 93 |

Without Catalyst/OI/One

TABLE 5

| No. | Presence of Cu and V | Substrate injected | C(NO$_x$) (mmol/kg) | R | T (° C.) | tr (min) | DC (mol %) | Yld (mol %) | Selectivity (mol %) |
|---|---|---|---|---|---|---|---|---|---|
| 13 | no | OI/One | 2.75 | 0.06 | 70 | 60 | 100 | 80 | 80 |
| 14 | no | OI/One | 30 | 0.58 | 70 | 60 | 100 | 85 | 86 |
| 8 | no | OI/One | 350 | 7.34 | 70 | 60 | 100 | 95 | 95 |

Without Catalyst/OI

TABLE 6

| No. | Presence of Cu and V | Substrate injected | C(NO$_x$) (mmol/kg) | R | T (° C.) | tr (min) | DC (mol %) | Yld (mol %) | Selectivity (mol %) |
|---|---|---|---|---|---|---|---|---|---|
| 15 | no | OI | 2.75 | 0.06 | 70 | 60 | 100 | 89 | 89 |
| 16 | no | OI | 30 | 0.62 | 70 | 60 | 100 | 91 | 91 |
| 18 | no | OI | 182 | 3.97 | 70 | 60 | 100 | 95 | 95 |
| 9 | no | OI | 350 | 7.94 | 70 | 10 | 100 | 95 | 96 |
| 19 | no | OI | 650 | 15.88 | 70 | 60 | 100 | 93 | 95 |

It is found that the selectivity is improved from the first addition of NOx. It is also found that, in the absence of catalyst, the selectivity increases more as the amount of NOx added goes up. A selectivity of more than 90% is reached, irrespective of the starting substrate, when at least 182 mmol/kg of oxides of nitrogen are added. For cyclohexanol, a selectivity of more than 90% is reached when at least 30 mmol/kg of oxides of nitrogen are added.

4. Conclusion

The process according to the invention therefore allows a degree of conversion of the organic substrate of 100% to be attained, while giving high yields of adipic acid and a significant selectivity, without the need to use catalyst.

The invention claimed is:

1. A process for preparing a dicarboxylic acid, the process comprising preparing the dicarboxylic acid having a structure of formula (I),

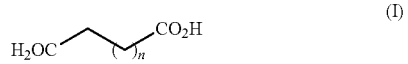
(I)

in which n represents an integer from 1 to 9, in a single step, by action of nitric acid, in the presence of one or more oxides of nitrogen selected from NO, NO$_2$, N$_2$O$_3$, N$_2$O$_4$, N$_2$O$_5$, NO$_3$, N$_2$O$_6$, N$_4$O and mixtures thereof, at a molar concentration in the reaction mixture of greater than 2.5 mmol of oxides per kg of reaction mixture, from a compound of formula (II) or (III) in which n represents the same integral number as in the formula (I)

(II)

(III)

wherein the nitric acid in aqueous solution is added in the reaction mixture and wherein said process uses a molar ratio R, corresponding to the number of moles of oxides of nitrogen added to the reaction mixture relative to the number of moles of substrate compounds (II) or (III) to be oxidized, and said radar ratio is gareater than or equal to 1.5.

2. The process as defined by claim 1, wherein the process comprises using a mixture of the compounds of formula (II) and (III).

3. The process as defined by claim 1, wherein n represents 3 or 9.

4. The process as defined by claim 1, wherein the molar ratio is greater than or equal to 2.

5. The process as defined by claim 1, wherein the oxide or oxides of nitrogen are NO or NO$_2$.

6. The process as defined by claim 1, wherein the amount of oxides of nitrogen is greater than 30 mmol/kg of the reaction mixture.

7. The process as defined by claim 1, wherein the amount of oxides of nitrogen is from 30 mmol/kg to 1000 mmol/kg of the reaction mixture.

8. The process as defined by claim 1, wherein the amount of oxides of nitrogen is from 30 mmol/kg to 850 mmol/kg of the reaction mixture.

9. The process as defined by claim 1, wherein the amount of oxides of nitrogen is from 180 mmol/kg to 650 mmol/kg of the reaction mixture.

10. The process as defined by claim 1, wherein the amount of oxides of nitrogen is from 300 mmol/kg to 400 mmol/kg of the reaction mixture.

11. The process as defined by claim 1, wherein the one or more oxides of nitrogen are employed in a gaseous form.

12. The process as defined by claim 1, wherein the process is carried out in the absence of a metallic oxidation catalyst.

13. The process as defined by claim 1, wherein the process is carried out using one or more oxidation catalysts.

14. The process as defined by claim 1, wherein the process is carried out at a temperature of from 20° C. to 150° C.

15. The process as defined by claim 1, wherein the process is carried out at a temperature of from 50° C. to 90° C.

16. The process as defined by claim 1, wherein the process is carried out with a total pressure in the mixture of from 1 bar to 30 bar.

17. The process as defined by claim 1, wherein the process is carried out with a total pressure in the mixture of from 1 bar to 4 bar.

18. The process as defined by claim 1, wherein the process comprises using NaNO$_2$ as a source of oxide of nitrogen.

19. A process for preparing a dicarboxylic acid, the process comprising preparing the dicarboxylic acid having a structure of formula (I),

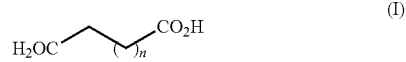
(I)

in which n represents an integer from 1 to 9, in a single step, by action of nitric acid in aqueous solution, in the presence of one or more oxides of nitrogen selected from NO, NO$_2$, N$_2$O$_3$, N$_2$O$_4$, N$_2$O$_5$, NO$_3$, N$_2$O$_6$, N$_4$O and mixtures thereof, at a molar concentration in the reaction mixture of greater than 2.5 mmol of oxides per kg of reaction mixture, from a compound of formula (II) or (III) in which n represents the same integral number as in the formula (I)
 (II)
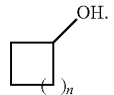 (III)
* * * * *